US012653469B2

(12) United States Patent
Nanke et al.

(10) Patent No.: US 12,653,469 B2
(45) Date of Patent: Jun. 16, 2026

(54) MAMMOGRAPHY SYSTEM FOR RECORDING AN X-RAY RECORDING DATASET, COMPRISING AN INTERRUPT UNIT, AND A METHOD THEREFOR

(71) Applicant: Siemens Healthineers AG, Forchheim (DE)

(72) Inventors: Ralf Nanke, Neunkirchen am Brand (DE); Steffen Kappler, Effeltrich (DE); Julia Wicklein, Erlangen (DE); Madeleine Hertel, Forchheim (DE)

(73) Assignee: SIEMENS HEALTHINEERS AG, Forchheim (DE)

( * ) Notice: Subject to any disclaimer, the term of this patent is extended or adjusted under 35 U.S.C. 154(b) by 261 days.

(21) Appl. No.: 18/475,629

(22) Filed: Sep. 27, 2023

(65) Prior Publication Data

US 2024/0099672 A1     Mar. 28, 2024

(30) Foreign Application Priority Data

Sep. 28, 2022     (DE) ..................... 10 2022 210 282.7

(51) Int. Cl.
| | |
|---|---|
| *A61B 6/04* | (2006.01) |
| *A61B 6/00* | (2024.01) |
| *A61B 6/03* | (2006.01) |
| *A61B 6/10* | (2006.01) |
| *A61B 6/50* | (2024.01) |

(52) U.S. Cl.
CPC ............ *A61B 6/0414* (2013.01); *A61B 6/032* (2013.01); *A61B 6/0487* (2020.08); *A61B 6/10* (2013.01); *A61B 6/502* (2013.01); *A61B 6/54* (2013.01)

(58) Field of Classification Search
CPC ....... A61B 6/0414; A61B 6/0487; A61B 6/10; A61B 6/502; A61B 6/54; A61B 6/025
See application file for complete search history.

(56) References Cited

U.S. PATENT DOCUMENTS

| | | | |
|---|---|---|---|
| 7,492,858 B2 | 2/2009 | Partain et al. | |
| 2008/0147398 A1* | 6/2008 | Kagermeier | ........... A61B 90/00 |
| | | | 704/E15.001 |
| 2008/0298536 A1 | 12/2008 | Ein-Gal et al. | |
| 2016/0367206 A1* | 12/2016 | Lee | ........................ A61B 6/502 |

(Continued)

FOREIGN PATENT DOCUMENTS

| | | | | |
|---|---|---|---|---|
| DE | 19741271 A1 | * | 5/1998 | ........... A61B 6/0421 |
| DE | 102008018266 A1 | | 10/2009 | |
| JP | H08196532 A | * | 8/1996 | |

OTHER PUBLICATIONS

Operator Manual Mammomat Inspiration (XPW7-330G.620.60.01.02).
Senographe Pristina mit Dueta , Screenshot Jul. 8, 2022 https://www.gehealthcare.de/products/mammography/pristina-dueta.

*Primary Examiner* — Casey Bryant
(74) *Attorney, Agent, or Firm* — Harness, Dickey & Pierce, P.L.C.

(57) ABSTRACT

One or more example embodiments of the present invention relates to a mammography system for recording an X-ray recording dataset of a region of interest of a breast of an examinee, comprising a compression unit for fixing the breast for the recording; and an interrupt unit triggerable by the examinee and connected to the compression unit and an X-ray source, the interrupt unit being configured to release the fixation and to stop the X-ray radiation.

18 Claims, 1 Drawing Sheet

(56)  References Cited

U.S. PATENT DOCUMENTS

| 2019/0150873 | A1 * | 5/2019 | Daum | ................... | A61B 6/032 |
| 2020/0289851 | A1 * | 9/2020 | Dilmanian | ........... | A61N 5/1042 |
| 2022/0031262 | A1 | 2/2022 | Cowles et al. | | |

* cited by examiner

MAMMOGRAPHY SYSTEM FOR RECORDING AN X-RAY RECORDING DATASET, COMPRISING AN INTERRUPT UNIT, AND A METHOD THEREFOR

CROSS-REFERENCE TO RELATED APPLICATION(S)

The present application claims priority under 35 U.S.C. § 119 to German Patent Application No. 10 2022 210 282.7, filed Sep. 28, 2022, the entire contents of which are incorporated herein by reference.

FIELD

One or more example embodiments of the present invention relates to a mammography system for recording an X-ray recording dataset, comprising an interrupt unit, and a method therefor.

RELATED ART

A mammography system comprises an X-ray source and an X-ray detector, wherein a breast is disposed between the X-ray source and the X-ray detector. The breast comprises a region of interest, in particular the entire breast. The breast is usually compressed or fixed in position via a compression unit. In particular, the surface of the X-ray detector or rather of a housing of the X-ray detector as well as a compression plate disposed essentially parallel thereto can be used for this purpose. Other forms of compression unit are also known. An X-ray recording dataset can be generated. Said X-ray recording dataset can include a full-field digital mammography recording or/and a tomosynthesis recording.

In mammography, the female (in some cases also male) breast is compressed for the X-ray examination for reasons of dose and image quality. This is usually done by lowering a compression plate until the desired compression of the breast against the detector table is achieved. Some women find this uncomfortable or painful. Moreover, there can be a feeling of loss of control on being "trapped" in the machine with no easy means of egress.

Modern mammography systems provide a tomosynthesis function to create a series of projections that allow three-dimensional imaging of the breast using reconstructed slices. In this process, the X-ray emitter/source sweeps the compressed breast at an angle of between 15 and 50 degrees. The full-field digital mammography recording and the tomosynthesis recording can also be contiguous within a compression. The inventors have identified the following problem: the lengthy scan/examination times resulting from tomosynthesis mode or combined mode involving digital full-field mammography recording and tomosynthesis recording, as well as the (sometimes rapid) movement of the emitter at head height, can further increase the patient's anxiety/stress level, so that panic reactions may occur in individual cases.

In known mammography systems, there are two emergency stop buttons, which are located on the pedestal and on the control panel and can only be pressed by the MTRA (medical-technical radiology assistant) in an emergency. This means that they cannot be actuated by the patient. In addition, the compression must be released manually by the MTRA. For example, a special button for emergency release must be pressed and the compression plate simultaneously pushed up manually for this purpose.

U.S. Pat. No. 7,492,858 B2 discloses a structure to be used for irradiating a body part, wherein the structure is designed to be positioned adjacent to a gantry rotatable about a horizontal axis and comprising a radiation source for generating a radiation beam, and a detector spaced at a distance from the radiation source and designed to be positioned between the body and at least a portion of the radiation beam and provided with an aperture designed to expose a body part extending therethrough to the radiation beam, wherein the structure comprises a holder for supporting the body part, wherein the holder is essentially cylindrical and comprises an end cap that is removable to facilitate positioning of a breast in the holder, and means for evacuating the holder. The structure further comprises a panic button connected to the evacuation means.

SUMMARY

One or more example embodiments of the present invention provides a mammography system for recording an X-ray recording dataset, comprising an interrupt unit, an associated method, as well as a computer program product and a computer-readable medium, giving the patient greater control and allowing them to release the compression of the breast at any time and abort the examination/recording in an emergency.

This is achieved by a mammography system for recording an X-ray recording dataset, comprising an interrupt unit as claimed in claim 1, an associated method as claimed in claim 13, as well as a computer program product as claimed in claim 15 and a computer-readable medium as claimed in claim 16.

BRIEF DESCRIPTION OF THE DRAWINGS

Exemplary embodiments of the invention will now be explained in more detail with reference to the accompanying drawings in which.

DETAILED DESCRIPTION

Figure 1:
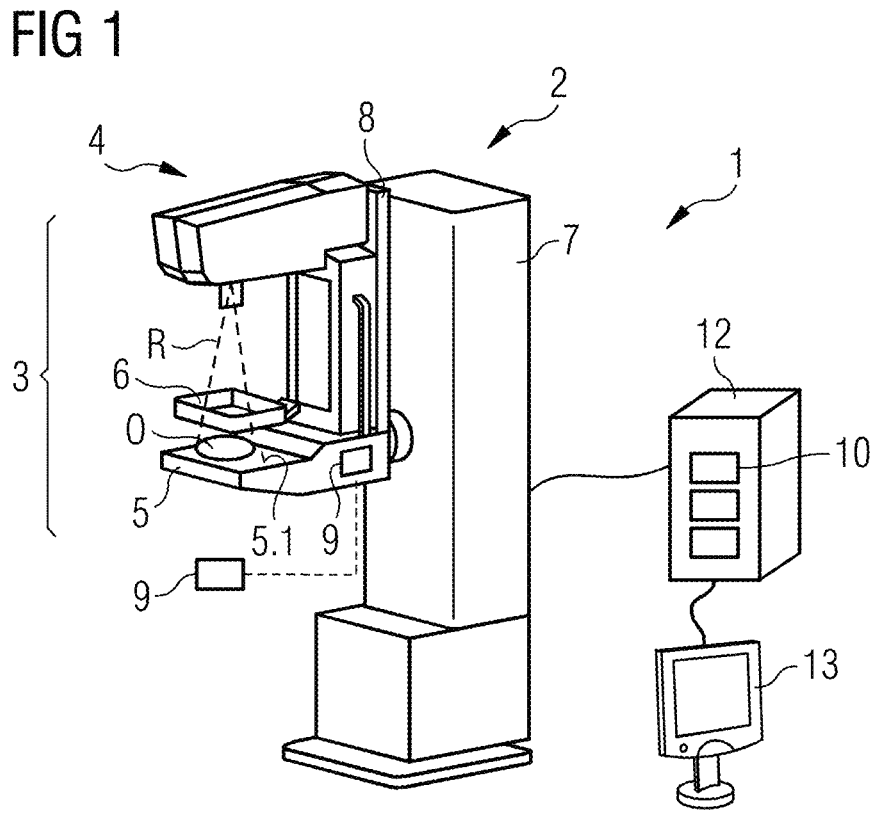
FIG. 1 schematically illustrates a mammography system according to one or more example embodiments of the present invention.

One or more example embodiments of the present invention relates to a mammography system for recording an X-ray recording dataset of a region of interest of a breast of an examinee, comprising:

a compression unit for breast fixation for recording, in particular between an X-ray source and an X-ray detector, an interrupt unit, which can be triggered by the examinee, connected to the compression unit and the X-ray source, said interrupt unit being designed to release the fixation and to stop, in particular abort, the X-ray radiation.

In particular, the mammography system can be designed to acquire a full-field digital mammography recording or/and a tomosynthesis recording. The full-field digital mammography recording or/and the tomosynthesis recording can be provided as an X-ray recording dataset. The X-ray source can be movable in an angular range of 15 to 50 degrees around the breast of an examinee. The breast of the examinee, in particular a female patient or in rare cases a male patient, is fixed in a compression unit between an X-ray source and an X-ray detector.

The interrupt unit can be triggered by the patient, i.e. patients can reach and activate the interrupt unit themselves.

The interrupt unit is connected to the compression unit and the X-ray source. The interrupt unit is designed to release the fixation and stop the X-ray radiation.

The inventors propose an interrupt unit, in particular in the form of a panic button, for a mammography and/or tomosynthesis system, which can be pressed by the (female or in exceptional cases male) patient in order to abort the examination.

By pressing the button, i.e. triggering the interrupt unit, the following take place immediately:

the breast compression is released, wherein the paddle or compression plate moves upwards, and the X-ray radiation is switched off, and the movement of the X-ray tube or source can be stopped or slowed down.

In contrast to the emergency stop buttons known today, in this invention the patients themselves have control over the panic button or rather the interrupt unit in order to abort/stop the examination at any time. When the interrupt unit is activated/triggered, in addition to stopping the X-ray radiation and the movement of the X-ray source, the compression of the breast in particular can also be released, allowing the patient to step back from the mammography system. The MTRA does not have to come to the system and perform an emergency manual release in order to "free" the patient. Advantageously, one or more example embodiments of the present invention provides a comprehensive approach for defined termination of the examination, in particular an approach that does not only involve releasing the fixation of the breast (by turning off the vacuum).

According to an aspect of one or more example embodiments of the present invention, the mammography system further comprises a motion unit for moving the X-ray source, wherein the interrupt unit is connected to the motion unit and is designed to stop the movement. In particular, the motion unit can be designed to acquire mammography recordings or more specifically full-field digital mammography recordings in different positions such as cranio-caudal (CC) or mediolateral-oblique (MLO), as well as tomosynthesis recordings. For example, the X-ray source can move within an angular range of 15 to 50 degrees.

According to an aspect of one or more example embodiments of the present invention, the motion unit comprises a switch unit or a brake unit that is triggered when the interrupt unit is triggered. The X-ray source can be stopped or rather the movement of the X-ray source can be prevented by de-energization or an active brake. The motion unit can be designed such that the motion unit is de-energized or actively braked by triggering of the interrupt unit. The motion unit can have a deceleration unit for performing continuous slowing to a stop and/or the motion unit can have a switch unit for abrupt stopping. The braking of the tube can be abrupt or at a defined speed, in particular to avoid causing more panic to the examinee. Abrupt can mean instantaneous, transitionless or sudden.

According to an aspect of one or more example embodiments of the present invention, the compression unit comprises a motor unit for performing continuous or gradual release and/or the compression unit has an abruptly releasable connection. The release of compression can be abrupt or at a defined speed, particularly so as not to cause further panic to the examinee. For example, the compression unit can comprise a releasable connection for releasing the fixation. The release can be performed abruptly or continuously.

According to an aspect of one or more example embodiments of the present invention, the interrupt unit is hardwired or wirelessly connected to control units of the X-ray source, compression unit and/or motion unit. In particular, in the case of a wireless connection, the connection can be designed to transmit a signal for releasing the fixation and stopping the X-ray radiation. The patient can hold a hardwired or wireless actuator in their hand, particularly during the examination or the recording. Alternatively, one or more actuators can be placed in readily accessible locations on the gantry or near the X-ray source or detector. For example, actuators can be provided for CC and MLO positioning.

According to an aspect of one or more example embodiments of the present invention, the interrupt unit comprises a protection unit to guard against inadvertent triggering. The trigger button or rather the interrupt unit can be protected against inadvertent actuation by a two-stage pressure switch, for example.

According to an aspect of one or more example embodiments of the present invention, the mammography system further comprises a biopsy protection unit designed to prevent triggering during an interventional process. The panic button/interrupt unit can be automatically disabled during interventional procedures in order to protect the patient from injury. For example, the interrupt unit function can be disabled as soon as a biopsy needle is present in the breast.

According to an aspect of one or more example embodiments of the present invention, the interrupt unit can additionally be triggered by a user. Optionally, the user, in particular the MTRA, can additionally have a corresponding possibility of pressing such a panic button, i.e. triggering the interrupt unit, independently of the patient/examinee. This can be advantageous, for example, if the patient/examinee is unable (or no longer) able to trigger the interrupt unit themselves. The user-triggerable interrupt unit can also be used to abort the examination in a controlled manner for other reasons, e.g. in the event of significant movement of the breast.

According to an aspect of one or more example embodiments of the present invention, the interrupt unit is connected to a system controller of the mammography system, designed such that the interrupt unit is automatically triggered if a system fault is detected. In the event of a system fault during a recording sequence or a recording, the interrupt unit and thus the release and stopping can be initiated automatically by the system controller, in particular without interaction of the examinee or user with the interrupt unit. Advantageously, a safe and preferably stress-free abort can be ensured. The interrupt unit can be directly connected to the system controller of the mammography system. The interrupt unit and/or the system controller and/or the connection between the interrupt unit and the system controller can be designed to trigger the interrupt unit in the event of a system fault.

According to an aspect of one or more example embodiments of the present invention, the compression unit comprises a compression plate, an air cushion, a tape or/and an adhesive tape. The interrupt unit can be used with conventional compression using compression plates. The interrupt unit can alternatively or additionally be used in any per se known methods of breast compression/fixation, such as deflation of an air cushion, release of holders for tape or other fixation means.

According to an aspect of one or more example embodiments of the present invention, the mammography system is designed to record a full-field digital mammogram (FFDM) or/and a tomosynthesis.

According to an aspect of one or more example embodiments of the present invention, the mammography system further comprises a fixation unit to prevent the examinee from falling when the interrupt unit is triggered. Depending on the system design, there may also be other patient fixation means, e.g. a back support, which can also be released by the interrupt unit. Alternatively or additionally, inflation of an airbag behind the patient can be activated by the interrupt unit to protect them from (fall) injuries, e.g. in the case of circulatory problems.

One or more example embodiments of the present invention further relates to a method for aborting recording of an X-ray recording dataset of a region of interest of a breast of an examinee using a mammography system, wherein the breast is fixed between an X-ray source and an X-ray detector using a compression unit, at least comprising the following step:

triggering of an interrupt unit which can be triggered by the examinee and is connected to the compression unit and the X-ray source, and thus releasing of the fixation and stopping of the X-ray radiation by the interrupt unit.

According to an aspect of one or more example embodiments of the present invention, a partial recording dataset taken prior to the releasing and aborting is made available as an X-ray dataset or as a basis for a repeat recording. If the abort occurs during a recording involving a plurality of partial recordings, such as a dual-energy recording, a previously acquired partial dataset can be used or displayed. For example, the partial dataset comprising a low-energy recording can be used as a full-field digital mammography recording dataset. For example, the partial dataset can be used as a so-called pre-shot for repeat recordings. In digital breast tomosynthesis, it can be automatically checked whether tomosynthesis reconstruction with a reduced number of projections is possible or useful, e.g. if the process is aborted after 23 of 25 projections. Advantageously, the dose of the aborted recording can be used. In particular, the mammography system can comprise a memory unit and computer unit in order to respectively store and process the X-ray recording dataset and the partial dataset.

One or more example embodiments of the present invention further relates to a computer program product comprising a computer program that can be loaded directly into a memory device of a controller of a mammography system according to one or more example embodiments of the present invention, having program sections for carrying out all the steps of a method according to one or more example embodiments of the present invention when the computer program is executed in the controller of the mammography system according to one or more example embodiments of the present invention.

One or more example embodiments of the present invention further relates to a computer-readable medium on which are stored program sections readable and executable by a computer unit for carrying out all the steps of a method according to one or more example embodiments of the present invention when the program sections are executed by the mammography system according to one or more example embodiments of the present invention.

FIG. 1 shows an exemplary embodiment of a mammography system 1 according to the invention, in particular in the form of a (breast) tomosynthesis system. Relative directional indications such as "above", "below", etc. refer to a mammography system 1 set up for operation as intended. The mammography system 1 comprises a recording unit 2 and a controller 12. The recording unit 2 has a pedestal 7 and a source-detector arrangement 3 which in turn comprise an X-ray source 4 and an X-ray detector 5 having a detector surface 5.1. During operation, the pedestal 7 stands on the floor. The source-detector arrangement 3 is movably connected to it so that the height of the detector surface 5.1, i.e. the distance from the floor, can be adjusted to a patient's breast height.

The patient's breast O (shown here schematically) lies with the region of interest for examination on the upper side on the detector surface 5.1. A compression plate 6 movably connected to the source-detector arrangement 3 is disposed above the breast O and the detector surface 5.1. For the examination, the breast O is compressed and fixed at the same time by lowering the compression plate 6 onto it so that pressure is exerted on the breast O between the compression plate 6 and the detector surface 5.1.

The X-ray source 4 is disposed opposite the X-ray detector 5 and is designed such that the X-ray detector 5 detects X-ray radiation R emitted by it after at least some of the X-ray radiation R has penetrated the breast O of the patient. Said X-ray source 4 can be pivoted relative to the X-ray detector 5 via a rotary arm 8, e.g. in a range of ±25° about a home position in which it is vertically above the detector surface 5.1.

The mammography system 1 for recording an X-ray recording dataset of a region of interest of a breast O of an examinee comprises a compression unit and an interrupt unit 9. The compression unit is constituted by the compression plate 6 and the detector surface 5.1. The compression unit is used to fix the breast between the X-ray source 4 and the X-ray detector 5. The interrupt unit 9, which can be triggered by the examinee, is connected to the compression unit, in particular the compression plate 6, and the X-ray source 4. The interrupt unit 9 is designed to release the fixation and stop the X-ray radiation R.

The interrupt unit 9 can be hard-wired or wirelessly connected to the controller 12, in particular for controlling the compression plate 6, the rotary arm 8 and the X-ray source 4. In one embodiment, the interrupt unit can be mounted on a housing that is preferably within comfortable reach of the patient/examinee. For example, the interrupt unit 9 can be provided on a housing of the X-ray detector 5 or X-ray source 4. Alternatively or additionally, the interrupt unit 9 can be implemented as a mobile operating unit. In particular, the interrupt unit 9 can comprise a switch or button or comparable input unit.

The mammography system 1 can in particular comprise a controller 12 and a computer unit. The controller 12 is connected to a terminal 13, e.g. comprising a user interface or display unit, via which a user can communicate commands to the mammography system 1 or retrieve measurement results, e.g. the X-ray recording. The controller 12 can be disposed in the same room as the recording unit 2, but can also be located in an adjacent control room or even more remotely.

In particular, the mammography system 1 can be designed to record a full-field digital mammography recording or/and a tomosynthesis recording. The full-field digital mammography recording or/and the tomosynthesis recording can be provided as an X-ray recording dataset. The X-ray source can be movable in an angular range of 15 to 50 degrees around a breast O of an examinee. The breast O of an examinee, in particular of a female patient or in rare cases a male patient, is fixed in a compression unit between an X-ray source 4 and an X-ray detector 5.

The interrupt unit 9 can be triggered by the examinee, i.e. examinees can reach and trigger the interrupt unit themselves.

The interrupt unit 9 is connected to the compression unit and the X-ray source 4. The interrupt unit 9 is designed to release the fixation and stop the X-ray radiation R. The interrupt unit 9 for a mammography system 1 and/or tomosynthesis system, in particular in the form of a panic button, can be activated by the female patient (or in exceptional cases the male patient) to abort the examination. Actuating the button, i.e. triggering interrupt unit 9, has the immediate effect of:

releasing the compression of the breast O, wherein the paddle or compression plate 6 moves upwards, and switching off the X-ray radiation R, and stopping or braking the movement of the X-ray tube, i.e. X-ray source 4.

The patients themselves have control of the panic button, i.e. of the interrupt unit 9, enabling them to abort or stop the examination at any time. When the interrupt unit 9 is activated or triggered, in addition to cessation of the X-ray radiation R and of the movement of the X-ray source 4, the compression of the breast O in particular can also be released, allowing the examinee to step back from the mammography system 1. The MTRA does not have to come to the mammography system 1 and perform an emergency manual release in order to "free" the patient.

The mammography system 1 additionally comprises a motion unit of the X-ray source 4, wherein the interrupt unit 9 is connected to the motion unit and is designed to stop the movement. The motion unit can in particular comprise the rotary arm 8. In particular, the motion unit can be designed to take mammography recordings or more specifically full-field digital mammography recordings in different positions, such as cranio-caudal (CC) or mediolateral-oblique (MLO), as well as tomosynthesis recordings. For example, the X-ray source 4 can move in an angular range of 15 to 50 degrees.

The motion unit has a switch unit or a brake unit which is triggered when the interrupt unit 9 is triggered. The X-ray source or rather the movement of the X-ray source can be stopped by de-energizing or by an active brake. For example, the rotary arm 8 can comprise a brake that can be controlled by the interrupt unit 9. Alternatively or additionally, the rotary arm 8 or rather the motion unit can be de-energized. The motion unit can be designed such that the motion unit is de-energized or actively braked by the triggering of the interrupt unit. The motion unit can have a deceleration unit for performing continuous cessation of movement and/or the motion unit can have a switch unit for abrupt cessation of movement. The braking of the tube or the X-ray source 4 can be abrupt or at a defined speed, in particular in order not to cause more panic to the examinee. Abrupt can mean instantaneous, transitionless or sudden.

The compression unit preferably has a motor unit for performing a continuous or gradual release. Alternatively or additionally, the compression unit has an abruptly releasable connection. The motor unit or/and the in particular abruptly releasable connection can in particular be associated with the compression plate 6, so that the fixation, i.e. compression, of the breast O can be released by, in particular, moving the compression plate 6 upwards. The compression can be released abruptly or at a defined speed, in particular so as not to cause even more panic in the examinee. For example, the compression unit can comprise a releasable connection for releasing the fixation. The release can be performed abruptly or continuously.

The interrupt unit 9 is hard-wired or wirelessly connected to control units of the X-ray source 4, the compression unit, in particular the compression plate 6, and/or the motion unit, in particular the rotary arm 8. The connection is schematically illustrated by way of example with a dashed line. The patient can hold a hard-wired or wireless actuator, in particular the interrupt unit 9, in their hand, in particular during the examination or the recording. Alternatively, one or more actuators, i.e. interrupt units 9, can be located at readily accessible locations on the gantry or rotary arm 8 or in the vicinity of the X-ray source 4 or X-ray detector 5. For example, actuators i.e. interrupt units, can be provided for the CC and the MLO positioning. By way of example, an interrupt unit 9 is shown schematically on the housing of the X-ray detector 5.

The interrupt unit 9 can preferably comprise a protection unit to guard against inadvertent triggering. The trigger button or rather the interrupt unit 9 can be protected against unintentional actuation e.g. by a two-stage pressure switch.

The mammography system further comprises a biopsy protection unit 10 designed to prevent triggering during an interventional step. The panic button/interrupt unit 9 is automatically disabled during interventional procedures in order to protect the patient from injury. For example, the operation of the interrupt unit 9 can be disabled as soon as a biopsy needle is inserted in the breast O.

The interrupt unit can preferably also be triggered by a user, in particular an MTRA. Optionally, the user, in particular the MTRA, can also have a corresponding possibility of pressing such a panic button, i.e. triggering the interrupt unit 9, independently of the patient/examinee. Triggering of the interrupt unit 9 by the user can also be used to interrupt the examination in a controlled manner for other reasons, e.g. in the event of significant movement of the breast O.

The interrupt unit 9 is connected to a system controller 12 of the mammography system 1 and is designed such that the interrupt unit 9 is automatically triggered if a system fault occurs. In the event of a system fault during a recording sequence or a recording, the interrupt unit 9 can be automatically triggered and thus the release and stopping can be automatically initiated by the system controller, in particular without interaction with the interrupt unit 9 on the part of the examinee or the user. The interrupt unit 9 can be directly connected to the system controller of the mammography system 1. The interrupt unit 9 and/or the system controller and/or the connection between the interrupt unit 9 and the system controller can be designed such that the interrupt unit 9 is triggered in the event of a system error.

The compression unit comprises a compression plate 6. The compression unit can alternatively or additionally comprise an air cushion, a tape or/and an adhesive tape (not shown). For conventional compression, the interrupt unit 9 can be used with compression plates 6. The interrupt unit 9 can alternatively or additionally be used in all per se known methods of breast compression/fixation, e.g. deflation of an air cushion, releasing of holders for tape or other fixation means.

The mammography system 1 is designed to record a full-field digital mammogram (FFDM) or/and acquire a tomosynthesis.

The mammography system 1 further comprises a fixation unit to prevent the examinee from falling when the interrupt unit 9 is triggered (not shown). Depending on the system design, further means for fixing the patient can also be provided, e.g. a back support which can also be released by the interrupt unit 9. Alternatively or additionally, inflation of an airbag behind the patient can be activated by the interrupt unit 9 to protect the patient from (fall) injuries, e.g. in case of circulatory problems.

Figure 2:
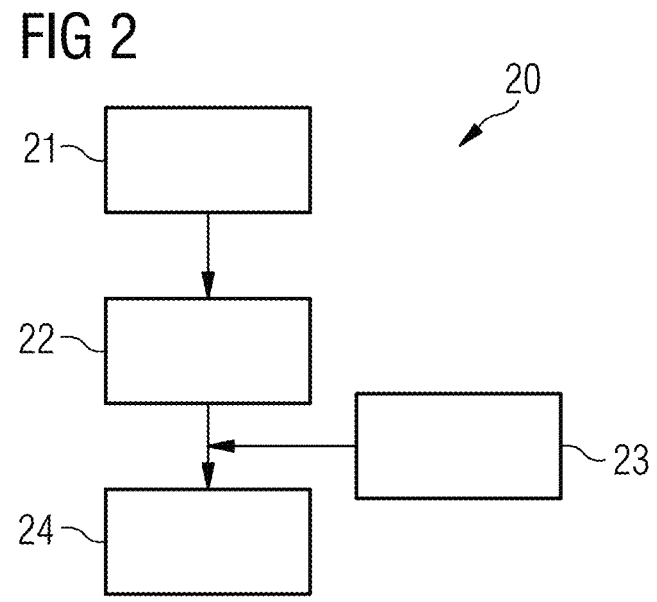
FIG. 2 schematically illustrates a method according to one or more example embodiments of the present invention.

FIG. 2 shows an exemplary embodiment of a method 20 according to the invention for aborting a recording of an X-ray recording dataset of a region of interest of a breast of an examinee using a mammography system, at least comprising the triggering step 23. The method 20 can further comprise the fixation step 21.

In a first fixation step 21, the breast is fixed between an X-ray source and an X-ray detector using a compression unit. In a subsequent acquisition step 22, X-ray recording can be started. In the triggering step 23, the interrupt unit, which can be triggered by the examinee and is connected to the compression unit and the X-ray source, is triggered, i.e. activated. This triggers release of the fixation and stopping of the X-ray radiation and thus termination 24 of the X-ray recording. A partial recording dataset obtained prior to the release and stopping is used as the X-ray recording dataset or as the basis for a repeat recording.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "on," "connected," "engaged," "interfaced," and "coupled." Unless explicitly described as being "direct," when a relationship between first and second elements is described in the disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" on, connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

It is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed above. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments. The present invention may, however, be embodied in many alternate forms and should not be construed as limited to only the embodiments set forth herein.

In addition, or alternative, to that discussed above, units and/or devices according to one or more example embodiments may be implemented using hardware, software, and/ or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/ hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one example embodiment relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

Although the present invention has been shown and described with respect to certain example embodiments, equivalents and modifications will occur to others skilled in the art upon the reading and understanding of the specification. The present invention includes all such equivalents and modifications and is limited only by the scope of the appended claims.

The invention claimed is:

1. A mammography system for recording an X-ray recording dataset of a region of interest of a breast of an examinee, comprising:
   a compression unit including at least one of a compression plate, an air cushion, a tape, or an adhesive tape, the compression unit configured to compress and fix the breast against a detector surface for recording;
   a motion unit including a rotary element configured to move an X-ray source; and
   an interrupt unit connected to the motion unit, the interrupt unit including at least one actuator, the at least one actuator configured to obtain a trigger request from the examinee, the interrupt unit connected to the compression unit and the X-ray source, the interrupt unit being configured to release fixation of the breast, cause movement of the motion unit and the x-ray source to stop, and stop X-ray radiation from the X-ray source upon obtaining the trigger request.

2. The mammography system of claim 1, wherein the motion unit comprises a switch unit configured to cause stopping of movement upon activation of a switch or a controllable brake which is activated when the interrupt unit is triggered.

3. The mammography system of claim 1, wherein the compression unit comprises at least one of, a motor configured to perform continuous or incremental release, or an abruptly releasable connection.

4. The mammography system of claim 1, wherein the interrupt unit is hard-wired or wirelessly connected to a controller configured to cause operation of at least one of the X-ray source, the compression unit or the motion unit.

5. The mammography system of claim 1, wherein the interrupt unit comprises a two-stage pressure switch configured to prevent triggering of the interrupt unit by a single touch to protect against inadvertent triggering.

6. The mammography system of claim 1, wherein
   the interrupt unit is configured to be disabled for a specified period of time to prevent a release of the breast during an interventional procedure.

7. The mammography system of claim 1, wherein the interrupt unit is triggerable by a user.

8. The mammography system of claim 1, wherein the interrupt unit is connected to a mammography system controller such that the interrupt unit is automatically triggered if a system fault is detected.

9. The mammography system of claim 1, wherein the mammography system is configured to record at least one of a full-field digital mammogram (FFDM) or a tomosynthesis.

10. The mammography system of claim 1, further comprising:
    a support configured to prevent the examinee from falling when the interrupt unit is triggered.

11. The mammography system of claim 1, wherein the compression unit comprises at least one of, a motor configured to perform continuous or incremental release, or an abruptly releasable connection.

12. The mammography system of claim 11, wherein the interrupt unit is hard-wired or wirelessly connected to a control unit of at least one of the X-ray source, the compression unit or the motion unit.

13. The mammography system of claim 12, wherein the interrupt unit comprises a two-stage pressure switch configured to prevent triggering of the interrupt unit by a single touch to protect against inadvertent triggering.

14. The mammography system of claim 13, wherein
    the interrupt unit is configured to be disabled for a specified period of time to prevent a release of the breast during an interventional procedure.

15. A method for aborting a recording of an X-ray recording dataset of a region of interest of a breast of an examinee by a mammography system, wherein a compression unit includes at least one of a compression plate, an air cushion, a tape, or an adhesive tape, the compression unit is configured to cause a fixation of the breast against a detector surface of an X-ray detector, the method comprising:
    triggering of an interrupt unit including at least one input interface configured to obtain a trigger request from an examinee, the interrupt unit being connected to the compression unit and an X-ray source;
    releasing, by the interrupt unit, the fixation upon obtaining the trigger request; and
    stopping movement of the X-ray source and stopping X-ray radiation upon obtaining the trigger request.

16. The method of claim 15, wherein a partial recording dataset obtained prior to the releasing and the stopping is made available as an X-ray recording dataset or as a basis for a repeat recording.

17. A non-transitory computer program product comprising a computer program, when executed by a controller of a mammography system, the controller having at least one memory device, cause the mammography system to perform the method of claim 15.

18. A non-transitory computer-readable medium having stored thereon program sections, when executed by a controller of a mammography system, the controller having at least one memory device, cause the mammography system to perform the method of claim 15.

* * * * *